United States Patent [19]

Craig et al.

[11] Patent Number: Plant 7,387

[45] Date of Patent: Dec. 4, 1990

[54] REGAL PELARGONIUM 'MAJESTIC'

[75] Inventors: Richard Craig, State College, Pa.; Glenn G. Hanniford, Worthington, Ohio

[73] Assignee: Research Corporation Technologies, Inc., Tucson, Ariz.

[21] Appl. No.: 337,783

[22] Filed: Apr. 10, 1989

[51] Int. Cl.[5] ..... A01H 5/00

[52] U.S. Cl. ..... Plt./68

[58] Field of Search ..... Plt. 68, 87.12

[56] References Cited

PUBLICATIONS

Greeting Card—Regal Geraniums "Crystal" series, developed by Dr. Richard Craig and Dr. Glenn G. Hanniford.

Craig, *Grower Expo,* "Stars Wars Approach to Designing the Perfect Regal Geranium", 1989.

*Penn Stater News,* "Photo of New Geranium to Appear on University Greeting Card", Dec. 1, 1988.

Penn State News Bureau, *Centre Daily Times,* "Geranium Chosen for Holiday Card", B-2, Dec. 11, 1988.

Peterson, *Penn Stater,* "Research Blossoms in Regal Debut", Penn State Alumni Association: 9-10, Jan.-/Feb. 1989.

*Primary Examiner*—Howard J. Locker

*Attorney, Agent, or Firm*—Scully, Scott, Murphy & Presser

[57] ABSTRACT

This invention relates to a new and distinct cultivar of regal Pelargonium (*Pelargonium*×*domesticum*) named 'Majestic' substantially as illustrated and described herein, particularly characterized as being compact and self-branching, early flowering and floriferous, and having medium red flowers with a ruby spot and feathering primarily on the upper petals.

2 Drawing Sheets

The present invention relates to a new and distinct cultivar of regal Pelargonium (*Pelargonium*×*domesticum*) called 'Majestic'. This cultivar is compact and self-branching (without pinching), early flowering and floriferous. The flowers are medium red with a ruby spot and feathering primarily on the upper petals.

The cultivar was developed from an organized, scientifically designed breeding program conducted at the Department of Horticulture, The Pennsylvania State University, University Park, Pa. 16802. The objective was to produce a new regal pelargonium genotype with excellent propagation characteristics, compact growth habit, predictable and consistent flowering response, and acceptable postharvest quality. 'Majestic' resulted from the selection from the progeny of the cross-pollination of regal Pelargonium cultivars 'Virginia' and 'Lavender Grand Slam'. The selection was asexually propagated by cuttings and the reproductions ran true.

With reference to the detailed description of the cultivar which follows, the test plant was potted in soilless medium and grown in a glasshouse under natural sunlight at a night temperature of about 58° F. and a day temperature of about 68° F. Fertilizer was applied in every watering, with 200 ppm nitrogen provided in the forms 15-16-17 (two consecutive) waterings) and 20-0-20 (every third watering) in a repeating cycle.

Figure 1:
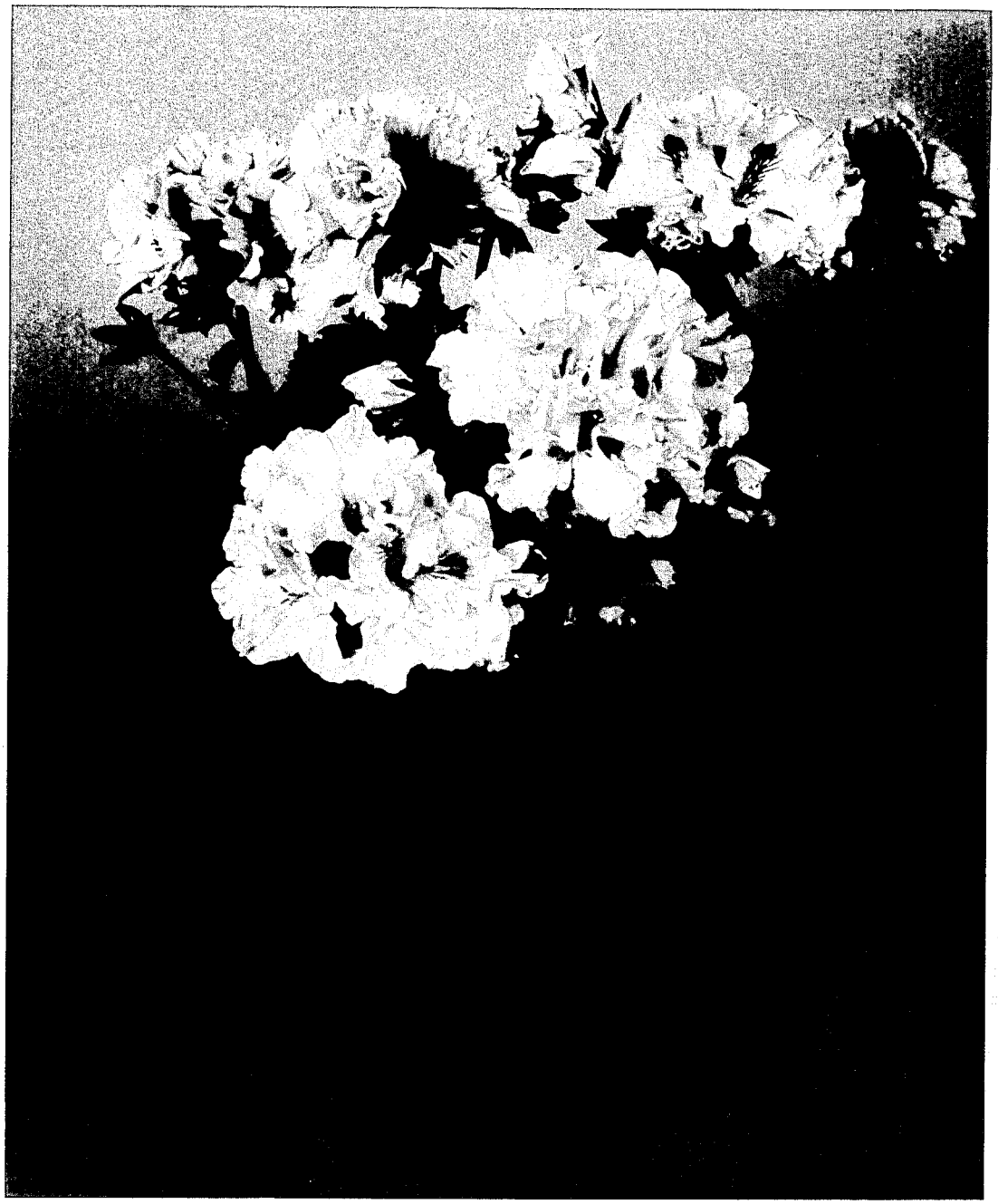
FIG. 1 illustrates in color the cultivar (cultivated with pinching) including foliage and flowers.
Figure 2:
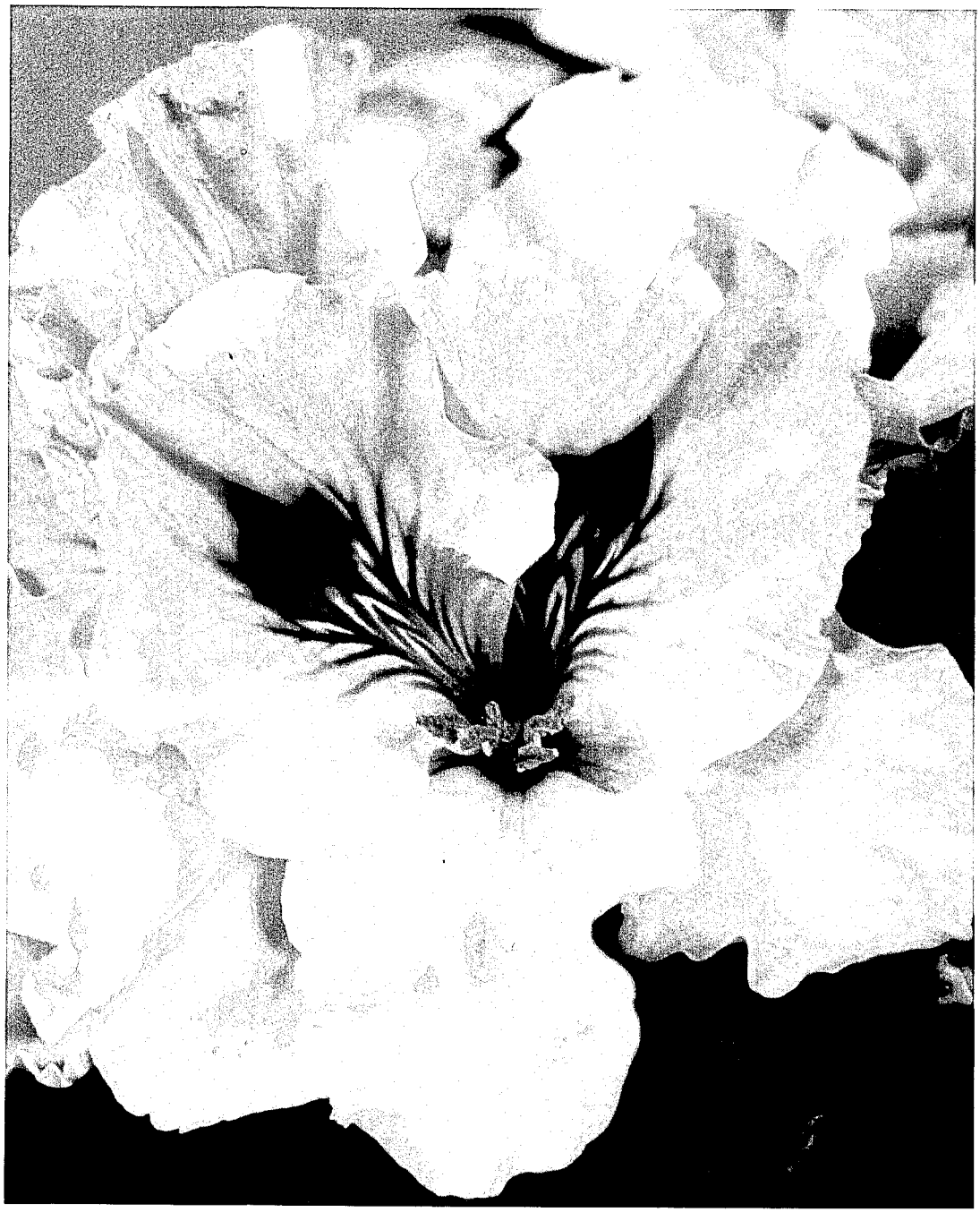
FIG. 2 illustrates in color primarily the floret.

Color readings were taken under cool white fluorescent light at approximately 200 foot candles and color identification was by reference to The Royal Horticultural Society Colour Charts, except where common terms of color definition are employed.

THE PLANT

Classification:

*Botanical.*—*Pelargonium*×*domesticum.*

*Tradename.*—#59-(78-4-1)='Majestic'

Form: Compact, self-branching.

Height: Approximately 20.0 cm [will vary with environmental and cultural conditions].

Leaves:

*Size.*—Largest leaf measured 11.0 cm across.

*Shape.*—Depressed ovate; base is cuneate to truncate to reniform; variously lobed; ratio of length to width is 2 to 3.

*Margin.*—Toothed.

*Texture.*—Pubescent.

*Color.*—Adaxial: Green 143C. Abaxial: Green 139D.

*Ribs and veins.*—Palmate venation.

*Petioles.*—Texture: Lightly pubescent. Color: Yellow-green 144A.

Stem:

*Internode length.*—Up to 1.5 cm.

*Color.*—Yellow-green 145B.

THE FLOWER

Blooming habit: Early and moderately floriferous, often comparable in earliness and inflorescence number to the cultivar 'Pink Gardener's Joy.'

Inflorescence form: Umbellate.

Inflorescence size: Varies with floret number; often 8-12 cm across (with florets fully open).

Disease resistance: Not known.

Florets:

*Number.*—5-9 per inflorescence.

*Form.*—Slightly cupped.

*Size.*—2.5-4.0 cm across.

Petals:

*Number.*—5 (on average).

*Texture and appearance.*—Smooth, reflective flecks; slightly ruffled edge.

*Color.*—Upper Petals: Adaxial: Margin: Red 52B. Central spot: Red-purple 59A. Proximal veins and feathering: Red-purple 61C. Abaxial: Margin: Red 52C. Central spot: Red-purple 54A. Proximal veins and feathering: Red 54A. Lower petals: Adaxial: Red-purple 58D. Abaxial: Red 55C.

Petaloids: None observed.

Sepals:

*Number.*—5 (on average).

Pedicel: Subtended by bracts.

*Length.*—Up to 3.0 cm.

*Color.*—Yellow-green 144B.

Peduncle: Arises from node; opposed to leaf petiole; subtended by leaves and bracts.

*Length.*—Up to 6.0 cm.

*Color.*—Yellow-green 144A.

REPRODUCTIVE ORGANS

Androecium:

*Stamens.*—Flat, ribbon-like filaments, joined at their bases; upper ⅓ of filaments is red-purple with white base; versatile attachment to anthers which are light purple and well developed.

Gynoecium:

*Pistil number.*—1. Length: 20.0 mm.

*Stigma.*—5–7-parted; red purple.

*Style.*—10.0 mm long; red-purple.

*Ovary.*—5.0–7.0 long; superior; very pubescent.

Fruit: Schizocarp; rarely observed.

What is claimed is:

1. A new and distinct cultivar of regal Pelargonium substantially as illustrated and described herein, particularly characterized as being compact and self-branching, early flowering and floriferous, and having medium red flowers with a ruby spot and feathering primarily on the upper petals.

* * * * *

UNITED STATES PATENT AND TRADEMARK OFFICE

CERTIFICATE OF CORRECTION

PATENT NO. : PP 7,387

DATED : December 4, 1990

INVENTOR(S) : Richard Craig, et al

It is certified that error appears in the above-identified patent and that said Letters Patent is hereby corrected as shown below:

Column 1, line 25: "forms 15-16-17" should read as --forms of 15-16-17--

Column 1, line 25: "consecutive) waterings)" should read as --consecutive waterings)--

Column 4, line 7: "red purple" should read as --red-purple--

Column 4, line 9: "5.0-7.0 long" should read as --5.0-7.0 mm long--

Signed and Sealed this

Twelfth Day of May, 1992

*Attest:*

DOUGLAS B. COMER

*Attesting Officer*

*Acting Commissioner of Patents and Trademarks*